United States Patent
Blount et al.

(10) Patent No.: US 11,911,173 B2
(45) Date of Patent: Feb. 27, 2024

(54) PRECLINICAL EVALUATION OF SKIN CONDITION AND RISK EVALUATION

(71) Applicant: DEB IP LIMITED, Derbyshire (GB)

(72) Inventors: Paul Blount, Derbyshire (GB); John Hines, Derbyshire (GB); Caroline Fellows, Derbyshire (GB); Chris Lang, Derbyshire (GB); Chris Mann, Derbyshire (GB); Kevin Ormandy, Derbyshire (GB)

(73) Assignee: Deb IP Limited, Derbyshire (GB)

( * ) Notice: Subject to any disclaimer, the term of this patent is extended or adjusted under 35 U.S.C. 154(b) by 495 days.

(21) Appl. No.: 16/649,958

(22) PCT Filed: Sep. 14, 2018

(86) PCT No.: PCT/GB2018/052619
§ 371 (c)(1),
(2) Date: Mar. 23, 2020

(87) PCT Pub. No.: WO2019/058100
PCT Pub. Date: Mar. 28, 2019

(65) Prior Publication Data
US 2020/0221993 A1    Jul. 16, 2020

(30) Foreign Application Priority Data

Sep. 25, 2017  (GB) .................................. 1715447

(51) Int. Cl.
*A61B 5/00* (2006.01)
*G16H 50/30* (2018.01)
*A61B 5/01* (2006.01)

(52) U.S. Cl.
CPC ............ *A61B 5/445* (2013.01); *A61B 5/0064* (2013.01); *A61B 5/015* (2013.01); *A61B 5/442* (2013.01);
(Continued)

(58) Field of Classification Search
CPC ......... A61B 5/445; A61B 5/443; A61B 5/442; A61B 5/7275; A61B 5/7264; A61B 2503/20; G16H 50/30
See application file for complete search history.

(56) References Cited

U.S. PATENT DOCUMENTS

| 2004/0059199 A1* | 3/2004 | Thomas | ................. | G16H 50/30 |
| | | | | 600/300 |
| 2009/0105550 A1* | 4/2009 | Rothman | ............... | G16H 50/30 |
| | | | | 600/300 |

(Continued)

FOREIGN PATENT DOCUMENTS

| WO | 2013021595 A1 | 2/2013 |
| WO | 2016057633 A1 | 4/2016 |

OTHER PUBLICATIONS

E. Held et al., "The hand eczema severity index (HECSI): a scoring system for clinical assessment of hand eczema. A study of inter- and intraobserver reliability," Contact Dermatitis, vol. 152, pp. 302-307, Jun. 2004 (Year: 2004).*

(Continued)

*Primary Examiner* — Joel Lamprecht
*Assistant Examiner* — Nyrobi Celestine
(74) *Attorney, Agent, or Firm* — McAndrews, Held & Malloy, Ltd.

(57) ABSTRACT

A system for quantifying risk associated with preclinical indicators of one or more clinical skin conditions, the system is formed of a plurality of measurement tools in connection with a processor, the measurement tools configured to various pre-clinical indicators of the skin health of a subject' hand, where the processor is configured to calculate a score based on the combined data from the plurality of measurement tools, this score being representative of the subject's risk of future development of one or more clinical skin conditions.

10 Claims, 2 Drawing Sheets

(52) U.S. Cl.
CPC ............ *A61B 5/443* (2013.01); *A61B 5/7275* (2013.01); *G16H 50/30* (2018.01); *A61B 2503/20* (2013.01); *A61B 2562/029* (2013.01); *A61B 2562/0233* (2013.01); *A61B 2562/0271* (2013.01)

(56) References Cited

U.S. PATENT DOCUMENTS

| | | | |
|---|---|---|---|
| 2015/0230712 A1* | 8/2015 | Aarabi | A61B 5/0077 600/476 |
| 2015/0254956 A1* | 9/2015 | Shen | A61B 5/445 340/573.1 |
| 2016/0100790 A1* | 4/2016 | Cantu | A61B 5/445 600/437 |
| 2016/0335910 A1* | 11/2016 | Baumann | G09B 5/00 |
| 2017/0270350 A1 | 9/2017 | Maltz | |
| 2017/0337345 A1* | 11/2017 | Pauws | G16H 50/20 |

OTHER PUBLICATIONS

K. S. Ibler, et al., "Skin care education and individual counselling versus treatment as usual in healthcare workers with hand eczema: randomised clinical trial", BMJ, pp. 1-14, Dec. 2012 (Year: 2012).*

P. van der Valk, et al., "A simple tool with which to study the course of chronic hand eczema in clinical practice," Contact Dermatitis, vol. 69, No. 2, pp. 112-117, 2013 (Year: 2013).*

PCT International Search Report for PCT Patent Application No. PCT/GB2018/052619 dated Jan. 3, 2019. 3 pages.

PCT Written Opinion for PCT Patent Application No. PCT/GB2018/052619. 10 pages.

* cited by examiner

PRECLINICAL EVALUATION OF SKIN CONDITION AND RISK EVALUATION

CROSS-REFERENCE TO RELATED APPLICATIONS/INCORPORATION BY REFERENCE

The present application is the U.S. national phase under § 371 of International Application No. PCT/GB2018/052619, having an international filing date of Sep. 14, 2018, which claims priority to GB Patent Application No. 1715447.7, filed Sep. 25, 2017. Each of the above-mentioned prior-filed applications is hereby expressly incorporated herein by reference in its entirety.

FIELD OF INVENTION

The invention relates to a system of diagnostic tools. Particularly, but not exclusively, it relates to a system for quantifying risk associated with measured preclinical indicators of one or more clinical skin conditions.

BACKGROUND TO THE INVENTION

It is known that monitoring of best hygiene practices reduces infection rates in healthcare environments. Such monitoring may be performed in real-time or as a series of snap shots over time where trends can be determined. Such monitoring principles also apply to skin care, where monitoring the correct use skin care produces helps to recognise and prevent skin conditions. This is particular relevant in occupational settings where workers may be exposed to a number of different of products which may affect a workers skin condition. It is known that occupational dermatitis within workers can lead to said workers requiring time off work, and therefore it is desirable to be able to monitor occupational skin health and condition.

Skin disease, and conditions associated with skin health, in particular hand skin health, is arguably the most common occupational disease, with occupational contact dermatitis (CD) accounting for up to 95% of all occupational skin disease; irritant contact dermatitis accounts for the majority of these cases. Contact dermatitis can have serious adverse impact on social and occupational aspects of life, including lost days at work, and threat to employment.

In order to develop a best practice of occupational skin care, it is necessary to assess skin health so as to recognise and monitor a multitude of skin conditions and link their prevalence with skin care practices. This has traditionally been difficult due to a reliance on self-reporting and the associated underreporting of skin health.

To this end, it is known for companies or facilities to perform skin condition audits. Typically such audits are performed on a voluntary basis, and provide a measure of the skin health of a particular individual. Such audits are largely performed visually and simply quantify the number and severity of apparent symptoms of bad skin, providing a one-off score which is only applicable to that particular subject. Further, current scoring methods tend to yield scores which group the majority of results together due to outlying data, limiting their usefulness in prompting action.

An object of the present invention is to mitigate some of the deficiencies of the prior art mentioned above.

STATEMENTS OF INVENTION

In accordance with an aspect of the invention, there is provided a system to quantify risk associated with preclinical indicators of one or more clinical skin conditions, the system comprising a plurality of measurement tools in connection with a processor, the measurement tools configured to measure at least two of erythema, scaling, papule density, vesicle density, infiltration, fissuring, surface hydration level, skin barrier function and transepidermal water loss of a subject, wherein each of the plurality of measurement tools is configured to provide a first score characteristic of the health of the skin of the subject's hand, and wherein the processor is configured to calculate a second score based on the combined first scores from the plurality of measurement tools, the second score representing the subject's risk of future development of one or more clinical skin conditions.

Accordingly, the present method codifies the combination of individual measurements into a global value, useable as a per-person hand skin health score and risk factor. By calculating a single number that characterises and summarises the combined data from a variety of measurement tools, themselves measuring a variety of skin health indicators, the present invention yields a concise and simple scaling output that allows a user to readily monitor their skin health (in particular, the skin of their hands), and allow for diagnosis of early indications of latent skin conditions and building them into a risk factor. Further, the standardisation of testing procedure and the use of measuring tools yields reliable, accurate and reproducible results that can be validly compared with prior or subsequent scores. The ability to identify hand skin conditions, and quantify the risk associated therewith, in a consistent manner may help in identifying and mitigating any risk associated with clinical hand skin conditions.

The invention allows for an early indication, and therefore likelihood, of a person, or facility, of suffering from a clinical skin condition such as occupational dermatitis. Such preclinical diagnosis provides an early indication of the user's hand skin condition and allows for both preventative and remedial action to be taken and best practice identified.

Optionally, the processor gives one or more of the first scores a different weighting in the calculation of the second score. By weighting different combinations of first scores, the second score can be tailored to gauge a particular skin condition or set of skin conditions.

Optionally, the system further comprises a plurality of subjects, wherein the processor combines the second score of each subject into a third score representative of the plurality of subjects. Combining the individual assessment data of a group of subjects into a single score allows for the hand skin health of a population to be summarised and tracked more easily.

Optionally, the plurality of subjects is representative of a larger population such that the third score can be mapped onto the larger population.

Optionally, the larger population is the total work force at a particular work site. Accordingly an entire facility can be monitored for changes in hand skin health that could indicate a systemic skin health risk linked to distinct occupational hazards particular to a given facility. Further, this provides a traceable facility or employer rating useful to monitor the base level skin health of their employees, identify sudden changes, long term trends and monitor the results of any treatments implemented on either particular individuals, groups or entire facilities.

Optionally, the plurality of measurement tools comprises one or more of a temperature sensor, humidity sensor, parallel and cross polarised light camera and a chromatic absorption sensor. This enables the claimed system to monitor the vast majority of physical attributes and symptoms that may indicate a range of skin conditions of varying degree. Furthermore, the provision of such instruments reduces the effects of user or operator bias that may otherwise be present when relying on human interpretation of visual indicators of skin health.

Optionally, the system further comprises a memory in communication with the processor, wherein the memory is configured to store data from multiple measurement sessions, and wherein the memory is further configured to provide data from past measurement sessions to the processor, and wherein the processor is configured to track changes in a score over time.

Optionally, the processor is further configured to recognise a trend in historical measurement data and predict future values of a score.

Optionally, the system further comprises indication means for alerting a user that a calculated score exceeds a predetermined threshold.

Accordingly, this provides an early warning capability for both individuals, groups of individuals and facilities with their associated populations. As such, an appropriate response can be triggered, the particular response depending on the threshold that was exceeded, as well as the particular skin health measurements that contribute to the scores.

Other aspects of the invention will be apparent from the appended claim set.

BRIEF DESCRIPTION OF THE DRAWINGS

Embodiments of the present invention will now be described, by way of example only, with reference to the accompanying drawings, in which.

DETAILED DESCRIPTION OF AN EMBODIMENT

In order to provide a system capable of quantifying risk associated with preclinical indicators of one or more clinical skin conditions, there is provided a system 10 in accordance to the present invention.

Figure 1:
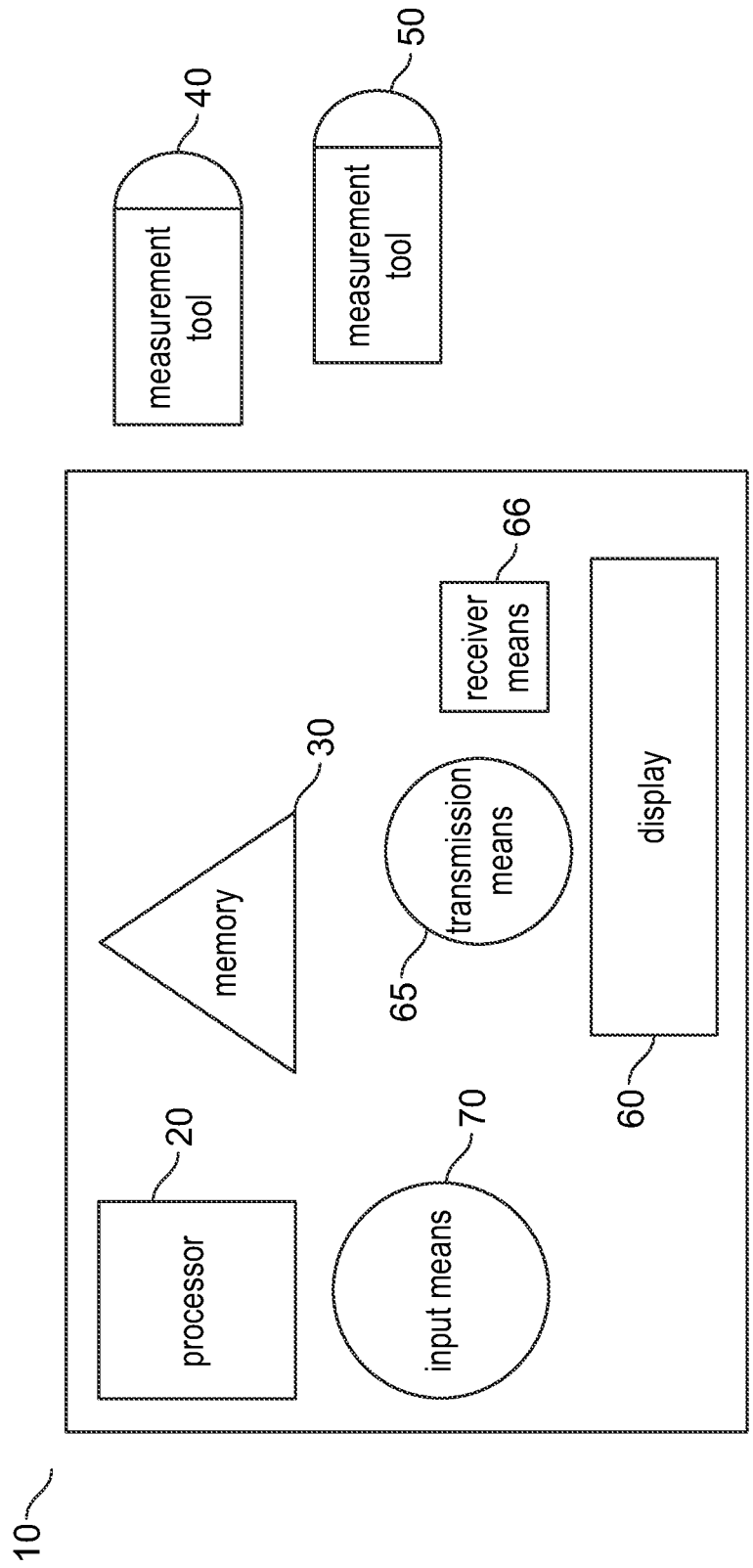
FIG. 1 is a schematic of a system in accordance with an embodiment of the invention.

FIG. 1 shows a schematic of a system 10. The system 10 comprises at least a processor 20, memory 30 and a measurement tool 40.

The measurement tool 40 is a known measurement tool configured to measure at least two of erythema, scaling, papule density, vesicle density, infiltration, fissuring, surface hydration level, skin barrier function and transepidermal water loss of a subject. In an embodiment, measurement tool 40 is provided by a plurality of separate devices 40, 50. In an alternative embodiment, measurement tool 40 is a single, multi-function device. Accordingly, in an embodiment the measurement tool 40, 50 is one or more of a temperature sensor, humidity sensor, parallel and cross polarised light camera and a chromatic absorption sensor.

The processor 20 is configured to receive data from the measurement tool 40, 50. In an embodiment, this data is raw measurement data. In an alternative embodiment, this data is in the form of a score characteristic of a component of the test subject's hand skin health. From this data the processor 20 is configured to calculate a user score based on the combined data or first scores from the plurality of measurement tools, the user score representing the subject's risk of future development of one or more clinical skin conditions.

The system 10 further comprises a form of memory 30, preferably non-volatile memory, and the processor 20 is configured to write data, such as the calculated scores to the memory 30. In an embodiment, the memory 30 is local. In an alternative embodiment, the memory 30 is an external database.

In an embodiment, the system 10 comprises input means 70. The input means 70 in an embodiment is an actuation means, in a preferred embodiment one or more buttons. In further embodiments the user input means is an alphanumeric keypad, with which the user may input one or more commands. As such any known suitable means for enabling a user to input a command to the system 10 may be used. Such input means 70 are known in the art.

Optionally, the system 10 further comprises a display 60, allowing measurement data and calculated scores to be communicated to a user. This display 60 in an embodiment is an LCD screen, in further embodiments any other known suitable means of display are used. The display enables an operator to input and review the scores of a test subject, or a number of test subjects. As described below, the results which are displayed on the display 60 may also be indicative of the score for an entirely facility, or several facilities.

Optionally, the system 10 comprises transmission means 65, allowing measurement data and data stored in memory 30 to be transmitted to a remote server for storage or further processing. In an embodiment, the system 10 further comprises receiver means 66, which may be used to update the memory with historical data, or alter the calculations made by the processor 20.

In use, the measurement tools 40, 50 are used to carry out a series of measurements on the skin of a user's hand. The particular measurements depend upon the specific measurement tools 40, 90 employed. Processor 20 calculates a user score from the data delivered by the measurement tool 40, 50. In an embodiment, the component data from each measurement tool 40, 50 is given an equal weighting so as to provide an aggregate score indicative of the overall health of skin of the user's hand. In an alternative embodiment, the data from each measurement tool 40, 50 is weighted differently such that the user score is indicative of the severity of a particular one or combination of skin conditions. The user score is written to memory 30.

The process of assigning a score is described in further detail below with reference to FIG. 2.

Thus the system of FIG. 1 allows for an automated and systematic collection of the data required to make the preclinical assessment of the skin condition. By performing the assessment utilising the system described, operator bias is substantially reduced as a weighted score is calculated in a systematic manner using equipment that produces accurate and reliable data. This further enables collected data to be validly compared with prior and subsequent date collected using the same system and equipment, improving the ability to recognise historical and forecasted trends.

A further advantage is that the system allows for the large scale collation of data. Whilst individual users are assigned a score providing an indication of their risk of future development of one or more clinical skin conditions, the score can be applied to a group of users within a facility or the entire facility itself. For example in a factory setting it may be useful to identify users according to their job or work environment, as office based workers may be less likely to suffer from certain conditions than workers on the factory floor.

Furthermore as the scores are generated and saved they can be viewed and visualised to identify trends over time, or by comparing different facilities, on both a user-by-user and workforce-wide basis. Furthermore, such visualisation may allow a skincare professional to identify best practice and monitor the impact of said best practice over time.

Advantageously scores can be compared to previously recorded scores stored in the memory 30. Thus trends for users, groups of users and facilities can be easily visualised over time. Furthermore, as the scores are weighted and calculated in a consistent manner, scores between different users, groups of users and facilities may be compared allowing for comparison between a predetermined target group and the measured group in order to determine and identify best practice.

Figure 2:
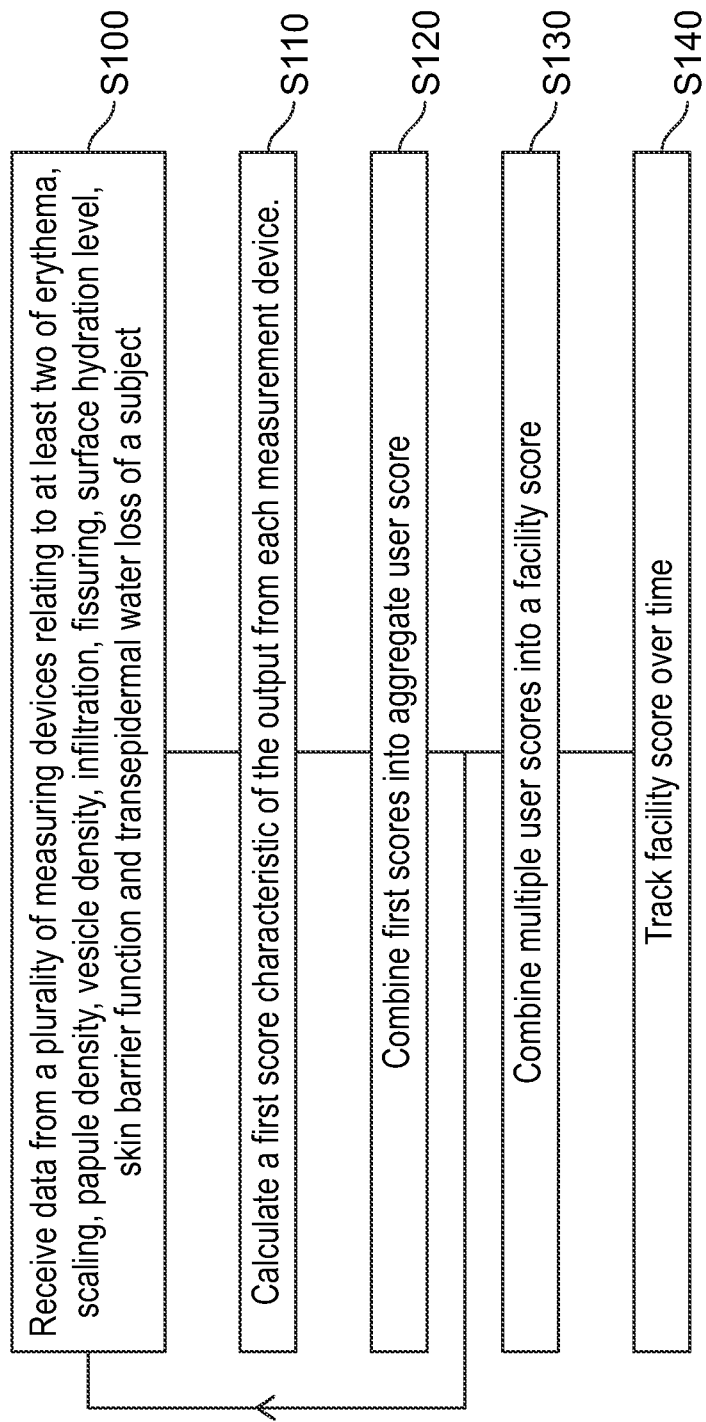
FIG. 2 is a flow chart of a method in accordance with an embodiment of the invention.

FIG. 2 shows a flow chart of the steps performed to calculate a score representative of a user's risk of future development of one or more clinical skin conditions.

The process commences at step S100. The system is initialised and the measurement tools 40, 50 are enabled and employed to measure physical attributes of a user's skin, including erythema, scaling, papule density, vesicle density, infiltration, fissuring, surface hydration level, skin barrier function and transepidermal water loss. In a preferred embodiment the attributes of a subject's skin are measured at their hand, thereby providing a hand skin measure. In further embodiments, other measures of a subject's skin attributes are measured at locations other than the subject's hands.

This data is then output to the processor 20 and optionally memory 30. The methods by which each attribute is measured are known in the art. For example, a preliminary visual assessment can be carried out covering six morphological signs of skin damage across eight different areas on the hands. The eight areas consist of the front of the fingers, the palms, the back of the hands and back of the fingers on both the left and right hand. If a morphological sign is observed in one out of the eight areas it scores one. If said sign is present in two areas, its scores two, and so on up to a maximum of three. When scoring fissures, a small flat fissure scores 1 and a deep fissure scores 3. Anything in between scores 2. A user can thus score between 0 and 18 in this one particular measurement, with 0 indicating good skin health.

Further measurement can be carried out using one or more of a temperature sensor, humidity sensor, parallel and cross polarised light camera and a chromatic absorption sensor. For example, Erythema is measured using a Mexameter, which uses light reflection to give L-A-B colour values. Five spot measurements are taken on the back of both the left and right hand, The Mexameter than outputs the average Erythema value across both hands, between 0 and 100.

Moisture content is measured using a Corneometer which relies on the capacitance method. A probe is brought into contact with a flat, hairless area of skin. This results in occlusion, as water is accumulated under the probe head, unable to evaporate. Again, five spot measurements are taken on the back of each hand of the user/test subject, yielding a score between 0 and 60.

Transepidermal water loss is measured by means of a Tewameter. The Tewameter operates on the open chamber measuring principle, whereby water evaporates through the chamber and the resulting density gradient is measured by two pairs of sensors. Here, the probe of the Tewameter is held in the area of skin between the thumb and index finger for thirty seconds before yielding a value between 0 and 20, 0 indicating the healthiest skin.

A Visioscope is used to assess scaliness. Scaliness is indicated by the number and thickness of skin flakes collected by a strip of corneofix tape. The tape is pressed on the skin of a user before being held to the Visioscope camera. The Visioscope then produces a value between 0-100% for scaliness.

At step S110, the processor 20 uses the data receives the data from each the measurement tools 40, 50 and calculates a first score characterising each physical attribute measured by the measuring tools. Optionally this first score is output to memory 30.

As the scores are measured using different range, (e.g. 0 to 100, 0 to 18 etc.) in an embodiment the scores for each test are scaled so that they are all measured along the same range, for example 0 to 10. Such scaling of the scores to the same range may make the calculation of the single score easier.

At step S120, the processor 20 combines each of the first scores into a user score, providing a concise, simple and actionable scaling output indicative of a user's global skin health. In an embodiment, each value outputted by each measurement device or method is normalised as a percentage of the total output, and the resulting values are averaged in order to provide an overall indicator of skin health. In an embodiment where the scores are scaled so as to be measured along the same range a total score may be recorded by summing the scores for each test. In a further embodiments, particular measurement devices or methods are identified as being more useful in the diagnosis of a particular skin condition or pre-condition of interest. In such embodiments these methods are therefore more heavily weighted in the calculation of the user score, which in turn provides measure of user's particular risk of having or developing the condition of interest. Thus the score would give a more reliable preclinical indication that a person may suffer from a particular condition.

The user score is then saved in memory 30.

Steps S100-S120 are then repeated for a number of distinct users, yielding a set of individual user scores for each user's hands. In an embodiment, these users form a statistically significant sample group of a larger population. In one embodiment, this larger population is the staff of a given institution or a particular facility.

At step S130, this set of user scores is combined into a single score representative of the sample group, and the larger population. Accordingly, for example, two hundred subjects might be measured at a factory with two thousand workers, producing a score applicable to the entire facility. Alternatively users may be subdivided into categories of interest, for example age, job, etc., and scores are assigned for each category. This facility or category score is saved to memory 30.

At step S140, the processor compares presently calculated values of first scores, user scores and facility scores with those stored in memory in order to identify trends in every level of the data (for example, individual users, user categories/groups and whole facilities) and avoid skin diseases/injuries by addressing latent risks at an earlier stage. These trends can be used to predict future values of a user, group of facility score. If a predicted score exceeds a predetermined threshold, the system can trigger an output, for example via display 60 or transmission means so as to prompt preventative action at the individual or facility wide level as required. In an embodiment, the scores outputted by the system 10 are transmitted to a remote server and displayed via an internet assessable dashboard, thereby enabling administrators to observe, assess and address the scores received by individual staff member and facilities remotely. This further facilitates the comparison and benchmarking of multiple subjects and facilities, which can be tracked and managed over time.

As such the present invention allows for a system that allows for an early preclinical determination of a skin condition by the use of multiple tests which are then scored. The total score gives a preclinical indication that a user may suffer from, or is showing signs of a skin condition, for example contact dermatitis. Advantageously, such a preclinical determination can be performed by a non-medical practitioner as it only requires the administration of the various hand tests, rather than analysis of the results.

The invention claimed is:

1. A system configured to quantify risk associated with preclinical indicators of one or more hand based clinical skin conditions, the system comprising a plurality of measurement tools in connection with a processor, each of the plurality of measurement tools configured to measure at least one property of the skin of a subject's hand, said property related to skin health, wherein the measurement tools are configured to measure at least two properties, comprising at least two of erythema, scaling, papule density, vesicle density, infiltration, fissuring, skin barrier function, surface hydration level, or transepidermal water loss of the subject's hand, provided that the at least two properties do not comprise the surface hydration level and the transepidermal water loss of the subject's hand, wherein each of the plurality of measurement tools is configured to provide a respective first score, wherein each first score corresponds to a respective property, wherein each of the plurality of first scores are normalized with respect to each other, wherein the processor is configured to calculate a second score based on the plurality of first scores, the second score representing the subject's risk of future development of one or more clinical skin conditions, wherein the system calculates a plurality of the second scores for a number of multiple subjects, wherein the number the multiple subjects comprise a statistically significant sample of a population within a work site, and wherein the processor is configured to determine a third score based on the plurality of the second scores to quantify risk associated with preclinical indicators of one or more hand-based clinical skin conditions for the work site.

2. The system of claim 1, wherein the processor is configured to weight one or more of the first scores differently in the calculation of the plurality of the second scores.

3. The system of claim 1, wherein the plurality of measurement tools comprises at least two of a temperature sensor, humidity sensor, parallel and cross polarised light camera, or a chromatic absorption sensor.

4. The system of claim 1, further comprising a memory in communication with the processor, wherein the memory is configured to store data from multiple measurement sessions, and wherein the memory is further configured to provide data from past measurement sessions to the processor, and wherein the processor is configured to track changes in a score over time.

5. The system of claim 4, wherein the processor is further configured to recognise a trend in historical measurement data and predict future values of a score.

6. The system of claim 1, wherein the system is further configured to alert a user that a score exceeds a predetermined threshold.

7. A method of quantifying hand skin health, the method comprising the steps of:

assessing the health of the skin of a subject's hand using a plurality of measurement tools, each of the plurality of measurement tools configured to measure at least one property of the skin of the subject's hand, said property related to skin health;

wherein the properties measured by the measurement tools comprise at least two of erythema, scaling, papule density, vesicle density, infiltration, fissuring, skin barrier function, surface hydration level, or transepidermal water loss of the subject's hand, provided that the at least two properties do not comprise the surface hydration level and the transepidermal water loss of the subject's hand in combination;

wherein the plurality of measurement tools are further configured to provide a respective first score, wherein each first score corresponds to a respective property;

wherein each of the plurality of first scores are normalized with respect to each other;

calculating a plurality of second scores based on the plurality of first scores, the plurality of second scores representing an overall health score of the skin on the subject's hand;

assessing the skin condition of a plurality of subjects;

calculating a third score representative of the plurality of subjects based on the second score of each subject;

wherein the plurality of subjects is representative of a larger population, further comprising the step of mapping the third score onto the larger population; and wherein the larger population is the total work force at a particular work site.

8. The method claim 7, further comprising the steps of repeating the assessment and calculation steps over time so as to track changes in at least one of the first, second or third score.

9. The method of claim 8, further comprising the step of recognizing a trend in historical measurement data and predicting future values of at least one of the first, second and third score.

10. The method claim 7, further comprising the step of alerting a user that a calculated score exceeds a predetermined threshold.

* * * * *